US005485230A

United States Patent [19]
Zimmerman

[11] Patent Number: 5,485,230
[45] Date of Patent: Jan. 16, 1996

[54] CHROMATIC MOTION DIAGNOSIS SYSTEM AND METHODS

[75] Inventor: George L. Zimmerman, New Orleans, La.

[73] Assignee: The Administrators of the Tulane Educational Fund, New Orleans, La.

[21] Appl. No.: 56,474

[22] Filed: May 3, 1993

[51] Int. Cl.$^6$ .................................................. A61B 3/02
[52] U.S. Cl. .................... 351/239; 351/242; 351/200; 351/243; 351/246
[58] Field of Search ................................. 351/239, 243, 351/224, 242, 200, 246

[56] References Cited

U.S. PATENT DOCUMENTS

| | | | |
|---|---|---|---|
| 3,922,554 | 11/1975 | Koloc | 250/461 |
| 3,927,323 | 12/1975 | Koloc | 250/329 |
| 4,634,243 | 1/1987 | Massof et al. | 351/243 |
| 4,848,898 | 7/1989 | Massof | 351/243 |
| 4,961,640 | 10/1990 | Irlen | 351/44 |
| 4,995,717 | 2/1991 | Damato | 351/224 |

OTHER PUBLICATIONS

Cavanagh P., "Attention–Based Motion Perception," *Science*, vol. 257, pp. 1563–1565 (Sep. 11, 1992).
Linsey et al., "Motion at Isoluminance: Discrimination/Detection Ratios for Moving Isoluminant Gratings," *Vision Res.*, vol. 30, No. 11, pp. 751–761 (Great Britian 1990).
Cavanaugh et al., "Color and Luninance Share a Common Motion Pathway," *Vision Res.*, vol. 25, No. 11, pp. 1595–1601 (Great Britian 1985).
Troscianko et al., "Why Do Isoluminant Stimuli Appear Slower?", *Optical Society of America*, vol. 5, No. 6, pp. 871–880 (1988).
Troscianko et al., "Phase Discrimination in Chromatic Compound Gratings," *Vision Res.*, vol. 28, No. 9, pp. 1041–1049 (Great Britian 1988).
Lee et al., "Contribution of Human Short–Wave Cones To Liminince and Motion Detection," *Journal of Physiology*, vol. (No.) 413, pp. 563–593 (Great Britian 1989).
Breitmeyer et al., "Effects of Isoluminant–Background Color on Metacontrast and Stroboscopic Motion: Interactions Between Sustained (P) and Transient (M) Channels," *Vision Res.*, vol. 30, No. 7, pp. 1069–1075 (Great Britian 1990).
Krauskoph et al., "Influence of Colour on the Perception of Coherent Motion," *Nature*, vol. 348, pp. 228–231 (1990).
Simpson, W. A., "The Use of Different Features By the Matching Process in Short–Range Motion," *Vision Res.*, vol. 30, No. 10, pp. 1421–1428 (Great Britian 1990).
Gorea et al., "Motion Processing by Chromatic and Achromatic Visual Pathways," *J. Opt. Soc. Am.*, vol. 6, No. 4, pp. 590–602 (1989).
Tyler, et al., "Purely Chromatic Perception of Motion in Depth: Two Eyes As Sensitive As One," *Perception & Psychophysics*, vol. 49(1), pp. 53–61 (1991).
Williams et al., "Perceptual Consequences of a Temporal Processing Deficit in Reading Disabled Children," *Journal of the American Optometric Assn.*, vol. 61, No. 2, pp. 111–121 (1990).

(List continued on next page.)

Primary Examiner—Viet Q. Nguyen
Attorney, Agent, or Firm—Olson & Hierl, Ltd.

[57] ABSTRACT

A system and method are described for determining a subject's perceived motion ability utilizing chromatic pathways. The equiluminant point between two selected colors is determined and two similar moving patterns are then provided, one equiluminant and the other luminant, the moving patterns consisting of only the two selected colors. The velocity of one pattern is held fixed while the velocity of the other pattern is matched to the fixed velocity by the subject. The difference between the matched velocity and the fixed velocity provides a measurement of the subject's perceived motion ability along the chosen chromatic pathways as compared to a standard. The comparison shows how to enhance motion perception ability by modifying the spectrum of the light impinging the subject's eyes in accordance with the comparison findings.

26 Claims, 6 Drawing Sheets

OTHER PUBLICATIONS

Cavanagh et al., "Perception of Motion in Equilumimous Kinematograms," *Perception*, vol. 14, pp. 151–162 (1985).

Scheiman et al., "Vision Characteristics of Individuals Identified as Irlen Filter Candidates," *J. An. Optom. Ass. Oc*, vol. 61, No. 8, pp. 600–605 (1990).

Cavanaugh et al., "Perceived Velocity of Moving Chromatic Gratings," *J. Opt. Sec. Am.*, vol. 1, No. 8, pp. 893–899 (1984).

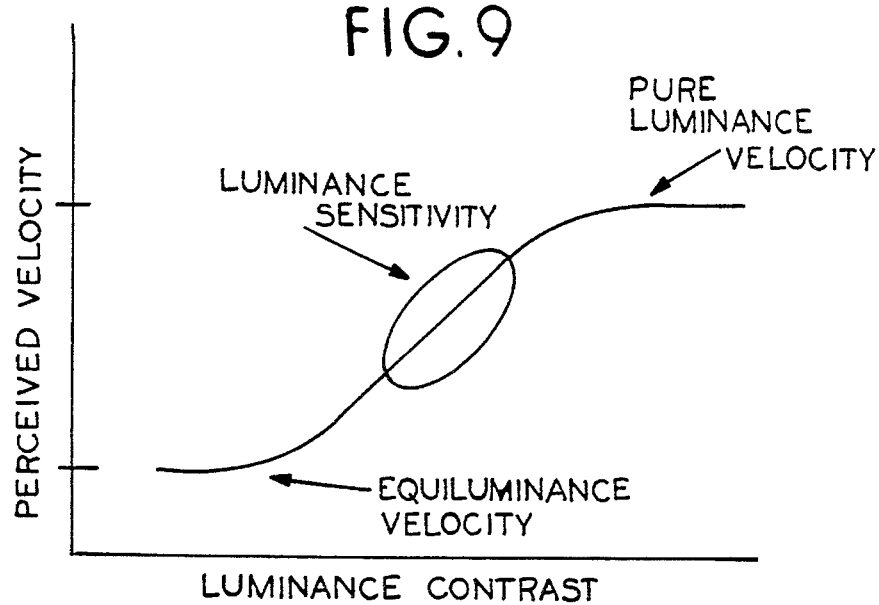
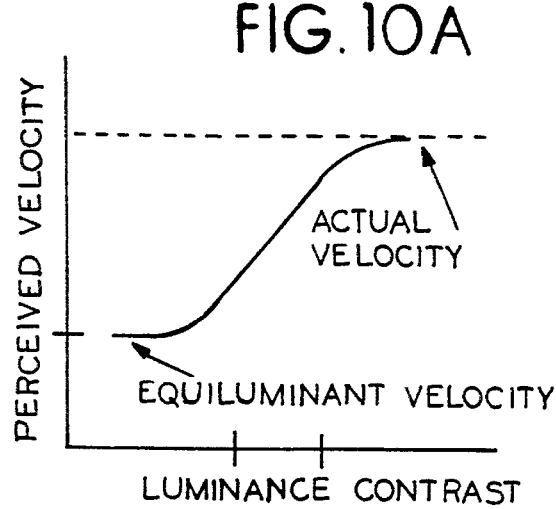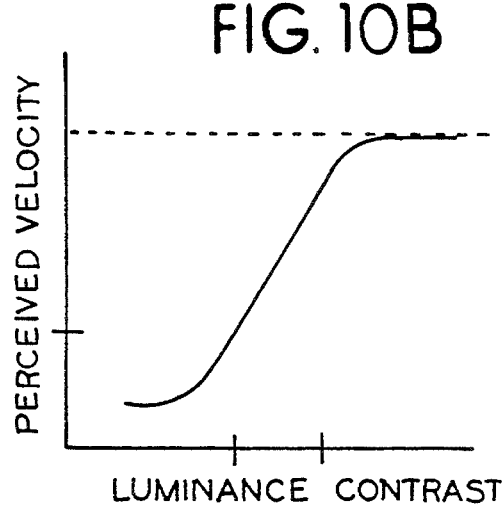
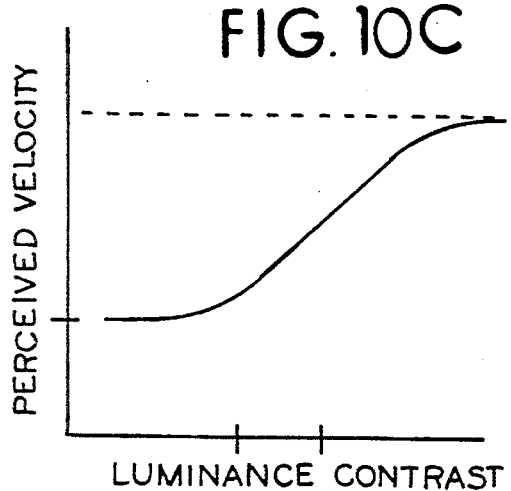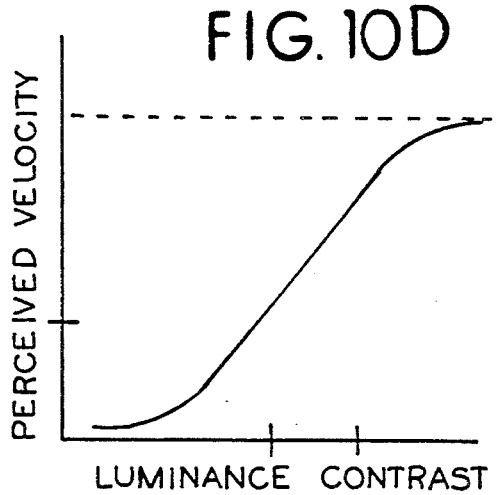

CHROMATIC MOTION DIAGNOSIS SYSTEM AND METHODS

TECHNICAL FIELD

The present invention relates to testing motion perception and enhancing motion perception, and specifically relate to methods which determine the ability of a subject to perceive motion through luminance and chromatic pathways in the brain. The invention can be used to detect individuals with special motion perception abilities or disabilities and enhance motion perception for an individual by modifying the spectrum of light impinging on the subject's eyes.

BACKGROUND OF THE INVENTION

Light which strikes the eyes of the individual is gathered by the retina and is converted into signals for transmittal to the brain. The brain processes those sensory signals to guide the thought and action of the individual. Thus, the perception of reality is a complicated combination of visual experiences and the neural structure of the brain.

Visual perception is the process of interpreting the surrounding environment with the eyes. The individual does not directly sense the surrounding environment, but only the reflective and ambient light which is present. The individual's knowledge of space, surface texture and movement is simply the most plausible interpretation of the complex patterns of light captured by the eyes.

The world which surrounds humanity is constantly in motion. An individual will move through the world while at the same time the world moves around the individual. The correct interpretation of the visual motion is critical to a virtual infinity of visually related tasks. Simple examples of everyday tasks requiring the accurate interpretation of visual information include driving a car, walking through a park, watching a movie or even reading a book. In addition, accurate interpretation of motion information is critical for optimum performance in athletic endeavors such as baseball, football, hockey, basketball, tennis, handball or soccer.

With regard to motion, the true velocity of an object is defined as the distance traveled by the object divided by the time it takes the object to move that distance. Surprisingly, the perception of that motion is not solely related to this true velocity of the moving object.

Perceived motion does not depend only on time and distance. When the luminance (brightness) of the light reflected from a moving object is matched to the luminance of the background, movement of the object will appear to slow down. This balanced state is called equiluminance. At equiluminance, all the information about the object and the background is carried by color differences.

The perceived slowing is due to the manner in which the brain processes information. At present, the exact physiological connections which make up motion perception are not precisely known. It is known that this phenomenon indicates the presence of multiple pathways or channels of motion information processing in the brain and that these channels seem to extract information from specific properties in the stimulus.

Perception begins with light impinging upon the rods and cones of the retina. Rods sense information under very low illumination levels. In normal daylight vision they are saturated and thus play no role in the phenomenon of equiluminance. The cones are separated into three types: red, green and blue. The cones on the retinas respond to a broad spectrum of light. Red cones are most sensitive to light in the red part of the visible spectrum. Green cones are most sensitive to light in the green part of the visible spectrum. Blue cones are most sensitive to light in the blue part of the visible spectrum.

The signals from the cones are roughly combined into three pathways as illustrated in FIG. 1 which are used to transmit the information to the brain. The first is an achromatic (or luminance) pathway which is formed by summing the signals generated by the red and green cones at a given location. The luminance pathway corresponds to the brightness or intensity of the impinging light.

The remaining two pathways are the red/green and the blue/yellow chromatic pathways. The red/green pathway is composed of the difference between the signals generated by the red and green cones at the given location. The blue/yellow pathway is composed of the difference between the summation of the red and green cone signals, namely, the luminance pathway, and signals generated by the blue cones at the given location.

For an average individual under normal lighting conditions, motion perception is dominated by the luminance pathway. Motion sensed along the chromatic pathways influences the overall perceived motion to a lesser extent. Under equiluminant conditions, no motion information is carried by the luminance pathway, isolating the chromatic pathways. When this happens, the motion perceived by the individual is slower than the perceived motion of an object with luminance information.

It is presently believed that the perceived motion of a pattern is comprised of information received from all three of the described pathways. The experimental evidence suggests that each person balances the input from each of the three pathways in a different manner. For example, the same moving pattern may produce different perceived velocities in different subjects depending on the particular combination of luminance and chrominance in the stimulus.

Accordingly, what is needed is a method of testing the motion perception signals from each pathway for a given individual. The method should also be able to provide an overall measurement of motion perception to allow diagnosis of special abilities or disabilities as compared to the general population. The method further should suggest measures to either enhance normal motion perception ability or improve the motion perception of disabled subjects.

The present invention meets those needs.

SUMMARY OF THE INVENTION

A method is described for testing the ability of a subject to perceive motion along the luminance and each of the chromatic pathways. Initially, an equiluminant point for two colors, such as either red/green or blue/yellow, is determined for each subject. Two moving patterns are then provided of the two selected colors. The only preferred structural difference between the moving patterns is that one carries the predetermined chromatic information point while the other carries luminant information.

The velocity of one moving pattern is fixed while the velocity of the other moving pattern is adjusted by the subject. The subject attempts to match the appearance of the adjustable velocity to the fixed velocity. The difference between the matched adjustable velocity and the fixed velocity provides a measurement of the relative perceived motion along the chosen chromatic pathway.

The balance between the luminance and chromatic pathways can be measured by various methods as disclosed. One such method uses a fixed velocity luminance pattern with a second pattern moving at the same velocity but in the opposite direction. The contrast of one pattern is fixed while the other is adjusted by the subject. The subject can vary the contrast of the luminance until the two patterns appear to be matched in velocity. This matching task is then performed for a second fixed velocity. The ratio of the difference in matching contrasts to the difference in the velocities provides a measure of the sensitivity of the motion perception to luminance changes. This provides a measure of the relative importance of each chromatic pathway to the overall perception of motion.

A comparison of the results to a standard derived from a given population allows for evaluation of the subject's ability versus that standard. The measurements also provide information which can be used to improve the motion perception ability of the subject by shifting the spectrum of light away from motion pathways which interfere the most with perception.

An individual's motion perception can be improved by adjusting the impact of luminant information over chromatic information. This is accomplished by modifying the illumination of the environment or shifting the spectrum of light impinging on the retina by having the subject wear tinted lenses. The adjustment involves measurement of the light spectrum in the environment of interest, measurement of the strength and balance of the motion sensing pathways, and, a process to find the best combination for the individual and the task.

BRIEF DESCRIPTION OF THE DRAWINGS

In the drawings which comprise a portion of this disclosure:

FIG. 9 is a diagram of perceived velocity versus luminance contrast;

FIGS. 10A, 10B, 10C and 10D are diagrams of the perceived velocity versus luminance contrast for various individuals;

DETAILED DESCRIPTION OF THE PREFERRED EMBODIMENT

Figure 1:
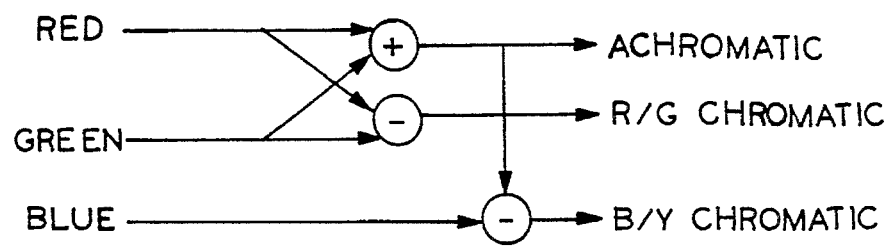
FIG. 1 is a schematic illustrating the luminance and chromatic visual pathways of human motion perception.

While this invention is susceptible of embodiment in many different forms, there is shown in the drawings and will herein be described in detail, one specific embodiment with the understanding that the present disclosure is to be considered as an exemplification of the principles of the invention and is not intended to limit the invention to the embodiment described.

Figure 2:
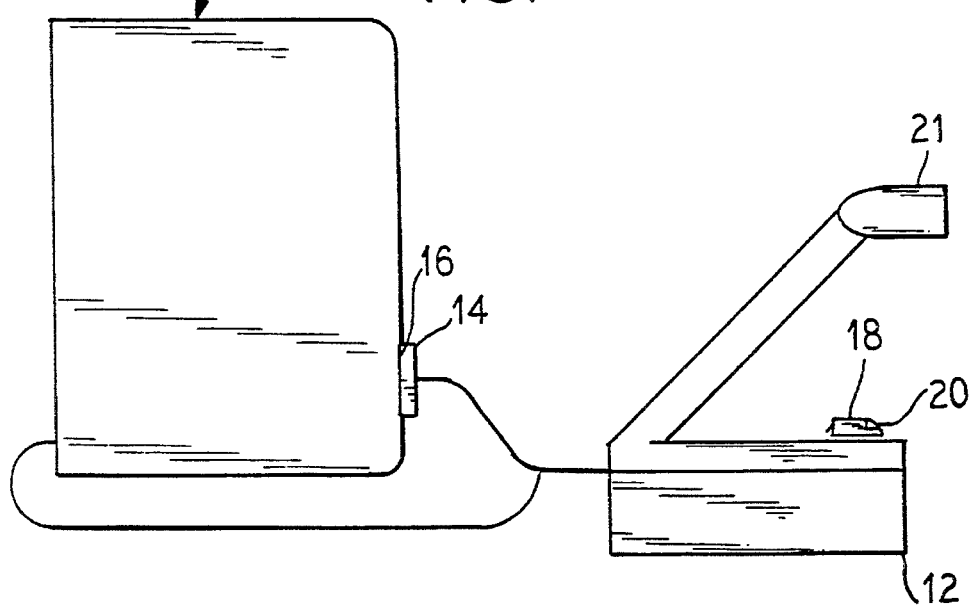
FIG. 2 is a perspective drawing showing the layout of one embodiment of the chromatic motion diagnostic system.

A color projector is preferably a color monitor 10 which uses an eight-bit videocard as best seen in FIG. 2. Other color projectors such as reflecting screens in combination with video projection systems will be apparent to those skilled in the art. The color monitor is a standard model which preferably utilizes three electron guns, one for controlling each of the three screen colors red, green and blue.

A voltage applied to any of the respective guns at a location on the monitor screen controls the intensity of the particular color at that particular location. The combination of the three color intensities at the location controls the color perceived by the eye at that location.

The color projector is electrically connected to a pattern generation system, preferably a computer 12, which controls the output of the color projector. Again, other pattern generation systems such as video tape players will suggest themselves to those skilled in the art.

To maintain constant linear color output both during the course of a single test and also from test-to-test, a monitor calibration circuit is preferably included within the pattern generation system, the monitor calibration circuit further having a photometer 14 and a memory in electrical communication. The memory is preferably a hard disk associated with the computer 12.

The hardware presently employed is a Macintosh IIci computer connected to two monitors. The second monitor is Macintosh high resolution 13-inch monitor driven by an eight-bit Macintosh videocard. The subjects responses are indicated through the motion of a mouse 18. The subject's eyes are held 57 cm from the screen by the use of a chin rest 21. All of the software is written in the programming language C and the interfacing with the videocard is done using a program called the Shell. The intensity of light is measured using a Lumex hand-held photometer. The light filters are constructed using Rosco lighting gels.

In the monitor calibration circuit, the pattern generation system puts a calibration pattern consisting of each of the colors red, green and blue onto a specific location 16 on the monitor 10. The photometer 14 is placed at that location 16 and the intensities of each color are continuously measured thereby and compared to the expected intensities which are stored in the memory. If the measured intensities and the stored intensities differ, the monitor calibration circuit adjusts the pattern generation system to compensate by altering the voltages applied to each electron gun. Thus, constant color output is linearized by matching the measured intensities to the expected intensities.

In the preferred embodiment, the calibration system extracts an estimate of the monitors gamma in each of the three guns—red, green and blue. The gamma is a singular value term that models the non-linear function of voltage for the gun versus the intensity of the light emitted by the monitor. The preferred embodiment generates a pattern of pixels and pixel energies which should have an average light intensity value that is equal if the gamma is chosen correctly. The gamma is adjusted continuously until the average values are equal. This gamma is found for each gun and used throughout the tests.

There are many patterns and energy levels that can be used to estimate the gamma which will be apparent to those skilled in the art. In the preferred embodiment, adjacent horizontal lines one pixel in width were used. Each alternate line is a different intensity level determined by the chosen gamma. The intensity of the output must be between 0 and 1. Let the alternating pattern be a combination of intensities a and b, such that a and b are constants that are between 1 and 0. If the average intensity for the pattern is 0.5 then the sum of a and b must equal 1. The gamma is the estimated 8 function. During the calibration, three different values for a,b are chosen for each gun color. If the gamma estimate is correct, the photometer will measure the same value for each a, b.

Means for adjusting the patterns generated on the color monitor is preferably a mouse 18 in electrical communication with the computer 12. The mouse 18 can be set to alter the parameters of the patterns as desired. These parameters include the velocity of moving patterns, the intensity of a pattern, the contrast of a pattern or the gamma. A clicker 20 is preferably provided with the mouse 18 to provide a signalling mechanism for the subject.

As discussed previously, the perception of motion is the result of how the brain of a given individual interprets the signals received along the three pathways. In general, the greatest weight is given to the luminance pathway while lesser contributions are received from the red/green and blue/yellow chromatic pathways. Also the perceived velocity of each of the pathways is different for each individual. The overall perceived motion in a given situation is a combination of the motion perceived along each pathway and the contributions of each pathway.

To generally determine a subject's ability to perceive motion utilizing only a chromatic pathway as compared to a luminance pathway, a first color and a second color are selected which determine the chromatic pathway. The equiluminant point of the subject with respect to the first and second colors is then found.

A first moving pattern is provided consisting of the first color and the second color with the colors being luminant with respect to each other. A second moving pattern is provided similar to the first pattern, except that the first and second colors are equiluminant with respect to each other.

Either of the first and second patterns is then maintained at a fixed velocity while the other pattern is provided with a means for adjusting its velocity. The subject then matches the appearance of the adjustable velocity to the fixed velocity.

Any difference between the matched adjustable velocity and the fixed velocity is a determination of the subject's perceived motion ability when utilizing only the selected chromatic pathway. To find the contributions of each chromatic pathway to the overall perception of motion a sensitivity test is performed. The contribution of the chromatic channel with respect to the luminance channel is something referred to as the luminance sensitivity of the channel. This is discussed in more detail below.

In one preferred embodiment, in order to test the contributions of the chromatic pathways versus the luminance pathway, the luminance pathway must be isolated from the chromatic pathways. To do so for the subject, the equiluminant point for that subject with respect to red/green or blue/yellow must be determined.

The equiluminant point for any two colors is defined as that point at which the perceived luminance of each color is equal. At the equiluminant point, no information regarding motion will be sent along the luminance pathway. Hence, only the chromatic pathways transmit motion information to the brain at equiluminance.

The equiluminant point can be found for the red/green pathway by manipulating the intensity of the two colors until the balance occurs. Since this is a perceptual phenomenon, a test that locates this point for each subject is preferably used. There are at least four observations that can be used to find the equiluminant point, namely, the slowing of perceived motion, the minimizing of flicker intensity, the diminishment of object depth, and the reduction of resolution. Any of these observations can be used with varying degrees of difficulty to find a subject's equiluminant point.

Figure 3:
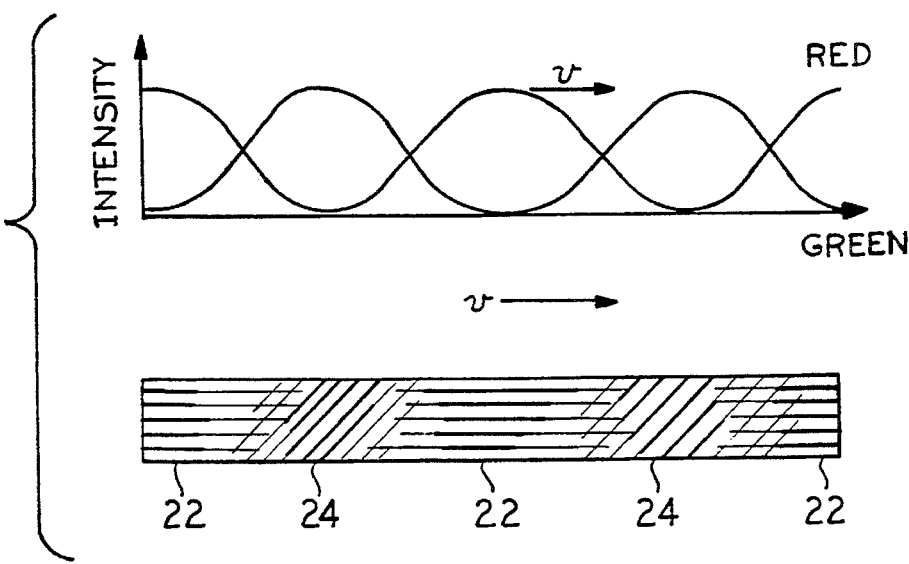
FIG. 3 shows one of the patterns generated on a monitor for determining the red/green equiluminant point.

For example, as seen in FIG. 3, a slowly moving (1 degree/second) pattern can be constructed through the pattern generation system by overlapping a red intensity sine wave pattern 22 with a green intensity sine wave pattern 24 180 degrees out of phase. The entire pattern will move at a given velocity shown in FIG. 3. If the contrast of one of the sine wave patterns remains constant and the contrast of the other is changed, a point will be reached where the intensities of the red and green sine wave patterns will be matched. When these intensities are matched, the subject will see the whole moving pattern seem to slow down and possibly stop. In the preferred embodiment, the subject would signal this point by activating the clicker 20. This is the red/green equiluminant point for the subject.

As another example, alternatively presenting a red pattern on a green background, and a green pattern on a red background will result in a flickering display. If one color is kept at a constant intensity value while the intensity of the other color is changed, there will be a point where the flickering will be minimized which the subject will again signal with the mouse clicker 20. This minimum point is the equiluminant point. This process of finding the equiluminant point is called heterochromatic flicker photometry.

Figure 4:
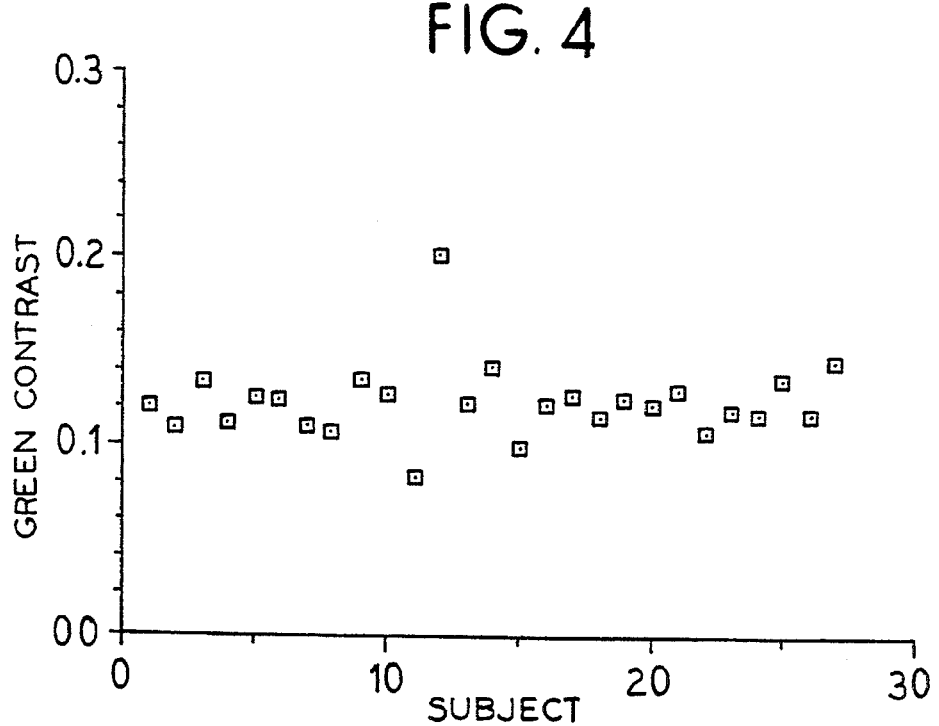
FIG. 4 shows the green contrast equiluminant points matched to 0.5 red contrast for a selected population.

A graph is presented in FIG. 4 which shows the equiluminant points for a group of individuals. In FIG. 4, the red contrast was held constant at 0.5 while the green contrast was varied. The results are shown.

The equiluminant points are used in all of the subsequent chromatic motion tests and will differ for each subject. Therefore, it is important to make a good estimate. The contrasts of the matched red and green intensities are stored for the rest of the examination.

To measure the relative motion perceived along each chromatic pathway demands that each of the chromatic pathways be isolated. As discussed previously, the pathways are created through two separate mechanisms which require two distinct methods for isolation. The first method is generally used to isolate the red/green pathway, but can in principle be used to isolate any two colors.

Similar to the equiluminant point determination, two patterns 26 and 28 are generated by the pattern generation system as shown in FIG. 5, each pattern using the two colors. Preferably, each pattern consists of two sinusoidal intensity patterns 22 and 24, one for each color, 180 degrees out of phase with each other. The colors for one pattern 26 will be at the predetermined equiluminant point while the colors for the second pattern 28 will not be at equiluminance.

To make the measurement, the subject utilizes the mouse 18 to adjust the velocity $v_{26}$ of the first pattern 26 until it is matched to the second pattern 28 which is maintained at a constant velocity $v_{28}$. Pushing the mouse 18 to the right speeds up the adjustable pattern 26 while pulling it to the left slows it down. The subject signals when the velocities $v_{26}$ and $v_{28}$ are matched via the mouse clicker 20. It makes little difference which pattern 26 or 28 the subject adjusts to perform the match, but there are some necessary restrictions on the patterns 26 and 28 and the velocities $v_{26}$ and $v_{28}$ of the patterns.

The moving equiluminant pattern 26 should have no distinct spatial frequencies above two cycles/degree. This is about the limit of resolution for the chromatic pathways. Any spatial component above two cycles/degree will only be detected by the luminance pathway, thus increasing the noise in the measurement.

In addition, motions below one degree/second will look stationary under equiluminant conditions. Therefore, it is important to make sure that the velocity $v_{28}$ being matched is greater than one degree/second.

Preferably, the pattern 28 to be matched maintains a constant rate of velocity $v_{28}$ of approximately three degrees/second. This velocity $v_{28}$ is to be fast enough so that the equiluminant pattern 26 can be seen to be moving while it is slow enough such that equiluminance will make a great difference in the perceived velocity $v_{26}$.

Since the luminance pattern 28 will have a motion pulling effect on the motion of the equiluminance pattern 26 if they are too close, the two patterns 26 and 28 are placed at a distance d such that the patterns 26 and 28 are separated by a three or four degree visual angle φ from each other to insure that the eyes of the subject must move in order to make the discrimination. This eliminates the pulling effect, thus, allowing for a good measurement.

The measurement patterns can take on many different shapes and directions to accomplish the same result. This will be apparent to those skilled in the art. Presently the measurement test is performed using the following pattern shapes to make similar measurements.

Figure 5A:
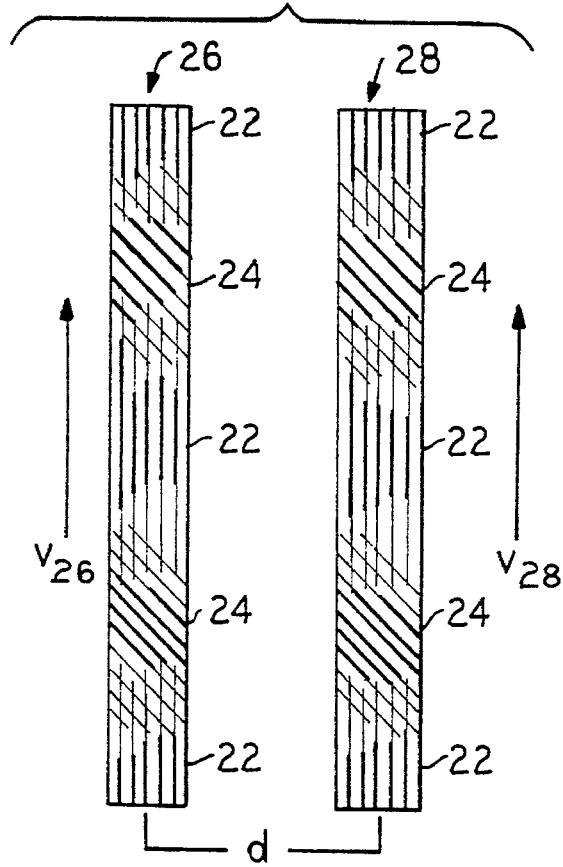
FIG. 5A and 5B show patterns generated on a monitor for determining the contribution of chromatic pathway to overall motion perception.
Figure 5B:
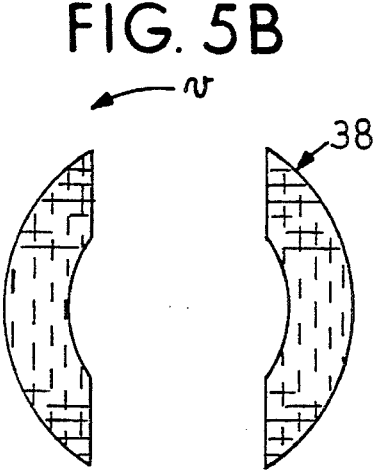

The fixed velocity and variable velocity patterns can move in either the same direction on the screen or in the opposite direction. The patterns can be either in straight lines as shown in FIG. 5A or curved forming a quarter of a circle as in FIG. 5B. The velocity direction and the pattern shape are used in all combinations for eliminating the effect of particular cues other than velocity that the subjects may be using to perform the task. Other patterns may be used to make the same measurement including different shapes, showing the different patterns in the same place at different times, and using a variety of different directions.

Figure 6:
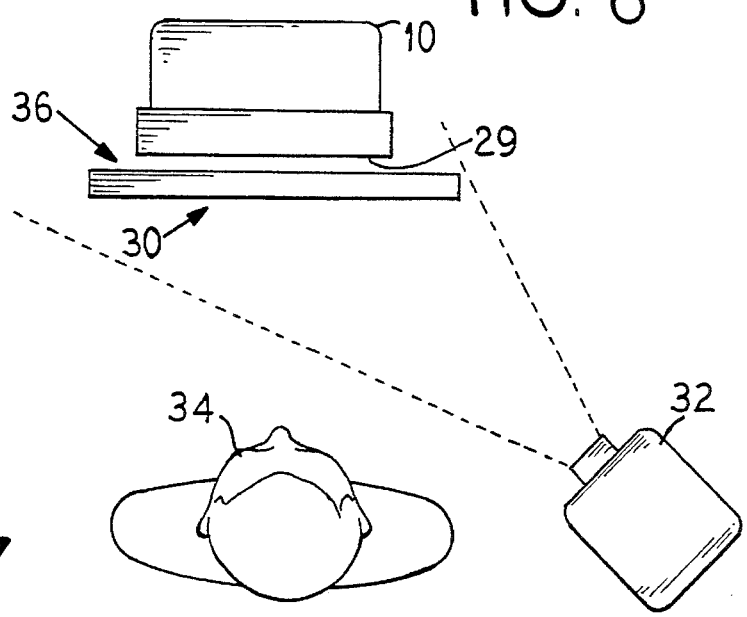
FIG. 6 is a perspective drawing showing the layout of a second embodiment of the chromatic motion diagnostic system.

The second method involves measurement of motion perception ability of the blue/yellow chromatic pathway and is best seen in FIG. 6. To do so, the preferred method will saturate the red and green cones of the retina and view the moving pattern through a blue filter. Such saturation will raise the visibility threshold for any differences along the red and green chromatic pathway. The blue filter will allow further reduction of the amount of red and green motion information sensed by the eyes. Thus, any motion information will only be perceived through the blue cones and hence only via the blue/yellow chromatic pathway. The saturation and filtering also minimizes the possibility that red and green information from other parts of the moving image will influence the luminance pathway.

Preferably, the part of the surface which is to be considered equiluminant needs to have a strong amber or yellow light reflecting into the subject's eye. This can be done by covering the surface 29 of the monitor 10 with a screen 31 of translucent material, preferably cheesecloth, and reflecting amber light from a strong amber light source 32 into the subject's eye 34. In addition, a blue filter 36 also covering the monitor surface 29 and having a spectral cutoff of about 550 nanometers is provided.

Alternatively, the saturation can also be done by using appropriate dichroic filters and a strong light source. It is the combination of the blue filter 36 and the strong amber light 32 which creates a situation where the moving image is "seen" only by the blue cones and hence by the blue/yellow chromatic pathway alone.

Figure 7:
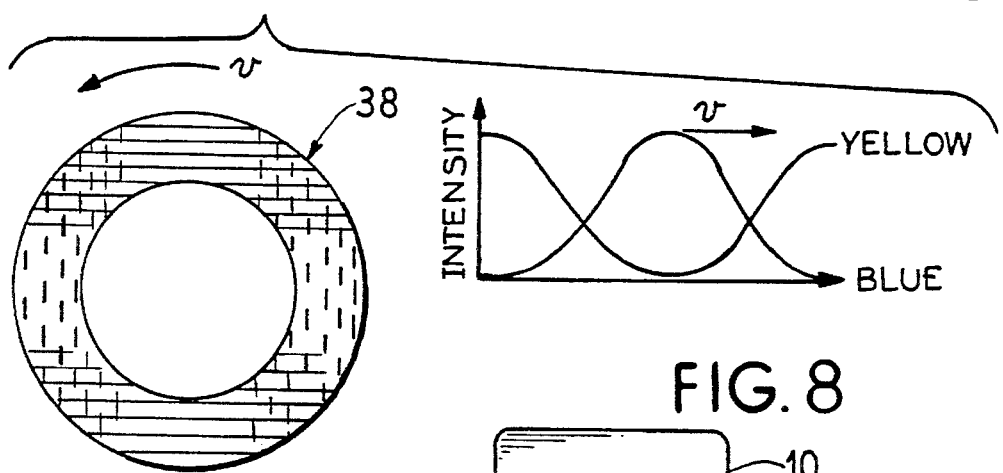
FIG. 7 shows one of the patterns generated on the monitor to determine the blue/yellow equiluminant point.

To determine the blue/yellow equiluminant point, a slowly rotating disk 38 as shown in FIG. 7 is displayed on the monitor surface 29 and is visible through the amber-illuminated screen. The blue/yellow equiluminant point is found by increasing the intensity of the impinging amber light source 32 until the moving pattern 38 is just visible through the translucent blue screen. At this point, the moving pattern 38 will appear to slow down or even stop. Unlike the red/green chromatic pathway, the blue cones contribute very little to the luminance pathway. This means that the individual's equiluminant point can be found by fully saturating the red and green cones with the amber light.

Figure 8:
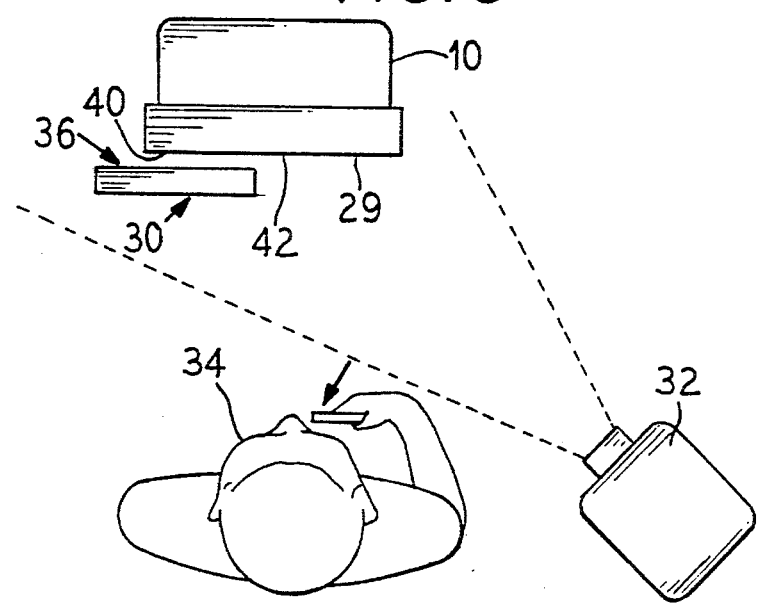
FIG. 8 is a perspective drawing showing a modification of the second embodiment of the chromatic motion diagnostic system.

To measure the relative motion ability perceived along the blue/yellow chromatic pathway, an equiluminant pattern and a luminant pattern are created. To do so, the translucent screen is positioned to occlude only the half of the monitor surface 29 where the equiluminant pattern 26 is situated as shown in FIG. 8. The equiluminant pattern generated is a high contrast black and white pattern. The non-occluded portion of the monitor surface 29 will contain the luminant pattern 28. The velocity matching is performed as described above for the red/green pattern.

The blue/yellow pathway is isolated by splitting the spectrum of light in the stimulus. The combination of the filter, translucent screen, and amber saturating light raise the threshold of visibility for the red and green cones of the subject and let through only information that can stimulate the blue cones. This effectively isolates the blue/yellow pathway. This method also can be effectively accomplished using dichroic filters which reflect light above about 550 nanometers and transmit light below 550 nanometers. Because there is a filter between the stimulus generating system and the eye, the pattern can take on many different actual colors. The only restriction is that the blue of the pattern is modulated.

The above relative motion measurements determine how each of the chromatic pathways perceive motion with respect to the luminance pathway. A pathway sensitivity measurement is used to determine the contribution of each pathway to the overall perceived motion ability.

This measurement is performed along each of the chromatic pathways independently by measuring how much luminance contrast will effect the motion of a purely chromatic pattern.

Methods to measure how much the luminance contrast will effect the motion of a purely chromatic pattern are described below. In general, for the red/green pathway, the equiluminant point between red and green is determined. A first pattern is provided having the red and green colors luminant with respect to each other. A second pattern similar to the first pattern is provided except that the red and green colors are equiluminant with respect to each other.

The first pattern and the second pattern are then superimposed over each other but are moving at fixed velocities in opposite directions. Either of the two patterns is held at a fixed contrast while the subject is provided with means to adjust a reference contrast of the other. The subject varies the reference contrast of the adjustable pattern until the whole pattern seems to stop. This measurement is made for two different fixed velocities to provide two reference contrasts, one for each velocity.

The ratio of the differences in reference contrasts to the differences in velocities is a measure of the sensitivity of the overall motion perception to changes in luminance. By comparing the determination to a pathway balance standard ratio provides an evaluation of the subject's ability with respect to the standard.

In one preferred method for the red/green chromatic pattern, the pattern generation system creates two moving patterns of red and green. One of the patterns is luminant and maintained at a fixed rate of velocity. The second pattern preferably consists of a equiluminant sinusoid maintained at a given velocity and in its same position a luminance pattern of variable contrast moving in the same direction at the same velocity. The velocity of the second pattern is chosen to be below the perceived matched velocity for the pathway but above the actual velocity of the luminant pattern. This measurement can be done for two velocities of the second pattern at ⅓ and ⅔ the difference between the perceived velocity of the red/green chromatic channel and the actual velocity of the test pattern. For a luminant pattern moving at 3 degrees per second and a perceived velocity of 6 degrees per second, the measurements can be taken at 4 degrees per second and 5 degrees per second.

When the luminance contrast of the second pattern is zero (this means that the second pattern is equiluminant) the pattern should be perceived to be moving slower than the first pattern. When the luminance contrast is high, the second pattern will be perceived to be moving faster than the first pattern. As the subject changes the contrast, there will be a point when the velocities of the two patterns will seem to be equal. This takes place at the reference contrast. A second velocity is then chosen. The ratio of the change in reference contrasts over the change in velocities is a measure of the sensitivity of the overall perception of motion to information from the red/green chromatic channel.

In general, for the blue/yellow pathway, the equiluminant point between blue and yellow is determined. A first moving pattern is provided having the blue and yellow colors luminant with respect to each other. A second moving pattern similar to the first pattern is provided except that the blue and yellow colors are equiluminant with respect to each other.

The first pattern and the second pattern are then superimposed over each other but are maintained at fixed velocities in opposite directions. Either of the two patterns is held at a fixed contrast while the subject is provided with means to adjust the reference contrast of the other. The subject varies the reference contrast of the adjustable pattern until the whole pattern seems to stop. This measurement is made for two different fixed velocities.

The ratio of the differences in the reference contrasts to the differences in fixed velocities is a measure of the sensitivity of the overall motion perception to changes in luminance. By comparing the determination to a pathway balance standard ratio provides an evaluation of the subject's ability with respect to the standard.

In another embodiment, the pathway balance between the luminance and either the red/green or the blue/yellow chromatic pathway can be determined. For ease of description, the blue/yellow pathway will be described. The subject is presented with a first moving pattern is which luminant and a second moving pattern which is equiluminant. The two patterns are of blue and yellow and similar and superimposed on each other. The first and second patterns are maintained at a first fixed velocity and are preferably moving in the same direction.

One of the first and second patterns is then set a first fixed contrast. For ease of explanation, the contrast of the first pattern will be considered fixed. The contrast of the second pattern is then adjustable by the subject to provide a reference contrast. A third pattern of the blue and yellow is also provided. The colors of the third pattern are luminant with regard to each other. The third pattern is maintained at a fixed velocity which is slower than the first fixed velocity but faster than the subject's perceived velocity of the second pattern.

The subject then adjusts the reference contrast of the second pattern until the first and second patterns appear to match the third pattern in velocity. This gives the first reference contrast. The first and second patterns are then set at a second velocity. The second velocity is chosen such that the previously fixed velocity for the third pattern is still slower than the second velocity but faster than the subject's perceived velocity.

The subject then adjusts the reference contrast until the first and second patterns appear to match the third pattern in velocity. This gives the second reference contrast. The ratio of the differences between the first and second contrasts to the differences in the first and second velocities is then determined. This provides a measure of the sensitivity of the overall motion perception to information from the blue/yellow chromatic pathway. As discussed above, this same procedure can be used for the red/green pathway.

In another preferred method, the sensitivity measurement for the blue/yellow chromatic pathway is determined by isolating the blue/yellow the pathway. The pattern generation system creates two moving patterns. The first pattern is maintained at a fixed rate of velocity. The colors used should be blue and black as described previously. The second pattern is a luminant pattern, preferably a high contrast black and white pattern and has a velocity slower than the first pattern. Isolation means are used to adjustable isolate the blue/yellow chromatic pathway from the first pattern. Referring to FIG. 8, this is preferably done with a blue filter 36 and an amber light 32 as discussed above. The subject then adjusts the intensity of the amber light until the two patterns appear to move at the same velocity. This provides the first reference measurement. The velocity of either the second or preferably the first pattern is changed and a second reference measurement is obtained as above.

The ratio of the difference of the reference measurements to the difference of the velocities is a measure of the sensitivity of the overall perception of motion to information from the blue/yellow channel. By comparing this determination to a pathway balance standard provides an evaluation of the subject's ability with respect to the standard.

The overall perception of motion for an individual is derived from the motion sensed along each of the pathways and the relative balance of the sensed motion. Each of the pathways will be presented with the same moving object. Each pathway interprets the motion differently. These different perceived motions are combined into a single interpretation according to a weighing that corresponds to the sensitivity of the pathway and the chromatic structure of the stimulus. The chromatic motion diagnostic system first isolates the motion sensing pathways, measures the motion sensed along each independent pathway, and then measures the sensitivity of the pathway to the overall perception. These measurements can determine how a person perceives movement for a given environmental situation.

The chromatic motion diagnostic system preferably gathers two pieces of information about an individual, namely, the relative motion perceived along each pathway and the contribution of that pathway to the overall perception of motion. Both the relative perception and the contribution seem to be highly variable between individuals and are intrinsic to the information processing abilities of the brain.

The motion perceived along each of the pathways is relative to the luminance pathway. The standard response would depend on the population being tested. From the information collected so far, the perceived motion with respect to luminance pattern moving at three degrees visual angle per second in the red/green chromatic pathway is 5 degrees per second and for the blue/yellow chromatic pathway is 4 degrees per second. The standard response for the pathway balance is 0.2 contrast-sec/deg for the red/green chromatic pathways and 1 cd-sec/m$^2$-deg for the blue/yellow chromatic pathway. The units for the red/green pathway are in terms of a contrast per velocity and the units for the blue/yellow pathway are in terms of an intensity per velocity. These measurements are proportional to the actual balance between the pathways.

An individual's ability to perceive motion can be characterized by the diagram in FIG. 9. FIG. 9 is the perceived velocity of an object versus the luminance contrast of the object with respect to a fixed color contrast. At equiluminance along the red/green pathway, for example, the perceived motion is at a minimum value. If the luminance contrast of the pattern is increased, the perceived velocity increases until it reaches the perceived velocity of a completely saturated luminant pattern. Between the two extremes in perceived motion, there is a transition region where the motion of the pattern changes with luminance contrast. The slope of this region indicates the sensitivity of motion perception to changes in luminance contrast of the pattern. This indicates how disruptive the chromatic pathways are to the individual's motion perception.

In the chromatic motion diagnostic system, the sensitivity of the luminance pathway is measured by measuring the slope of the psychometric function shown in FIG. 9. A chromatic and luminance combined pattern moving at two different rates of speed is matched to a luminant pattern maintained at a constant rate. The speed of the combined pattern for this test is ⅓ the difference and ⅔ the difference between the matched velocity and the actual velocity of the pattern. This places these measurements right on the slope of the psychometric function.

Using the same methods, it is possible to either make more measurements in order to increase the resolution of the individual's psychometric function along the given chromatic pathway or search for a threshold measure that incorporates in formation about the slope of the psychometric function.

FIGS. 10A, 10B, 10C and 10D are diagrams of possible psychometric functions of an individual for a single chromatic pathway. Each graph denotes perceived velocity on the vertical axis and luminance contrast on the horizontal axis. FIG. 10A represents a normal pathway response for comparison to FIGS. 10B, 10C and 10D which are all chromatic pathway conditions which could give rise to problems under certain stimulus conditions.

FIG. 10B shows a chromatic pathway for a subject who senses motion significantly slower than normal at equiluminance. Because the graph has a slope much steeper than normal, this individual would be able to function normally under most lighting situations. Motion perception problems would occur when conditions approached equiluminance. Another way of stating this is to notice that the steep slope of the psychometric function depicted in FIG. 10B indicates that this chromatic channel contributes little to the overall perception of motion with respect to the luminance channel.

FIG. 10C shows a chromatic pathway for a subject who senses motion at the same velocity as normal but the slope of the psychometric function is much shallower. The shallow slope suggests that the chromatic channel contributes significantly to the overall perception of motion with respect to the luminance channel. Motion perception difficulties would arise under changing lighting conditions.

FIG. 10D shows a chromatic pathway for a subject who has both a shallow slope and senses motion slower than the normal chromatic pathway. This individual would have an overall poor perception of motion under normal lighting conditions. Changes in chromatic content would dramatically change the perceived motion even though the actual motion remained constant. This will introduce perception which would not exist to the same extent in a person with the normal chromatic pathway response.

The chromatic motion diagnostic system provides an estimate of the psychometric function depicted in FIG. 10. The measurement of the relative motion perceived along a given chromatic pathway sets the lower bound on the psychometric function. The upper bound is the actual motion of the luminant pattern. The channel balance measurement provides an estimate of the slope of the psychometric function for a given chromatic channel. Measurements for the two chromatic channels with respect to the luminance channel characterize an individual's motion perception abilities for a broad spectrum of conditions.

One important item to note from the graphs of FIG. 10 is that even the normal individual depicted in FIG. 10A will sense motion slower at equiluminance. By reducing the impact of the chromatic channels on the subject's environment, it is possible to improve the motion perception of the normal individual also.

However, if the luminance pathway were deficient in some manner, selection of the appropriate spectrum of light to impinge upon the subject's retina based upon the smallest difference in matched adjustable velocity and fixed velocity would improve the motion perception abilities of the subject.

These graphs provide methods of correcting disabilities and enhancing abilities for each individual. For example, there are several ways to modify the spectral content of the impinging light to influence the individual's ability to perceive motion. If the individual is working within a structured environment, the illumination of the environment could be changed to improve motion perception.

An alternate way of modifying the spectral content of the light impinging on the retina is to have the individual wear tinted contacts or glasses. The choice of color of tint in this case would depend on the spectral content of the light where the lenses are to be used and the measurements of the individual's chromatic motion perception.

If the major contributing factor of an individual's deficient motion perception is along the blue/yellow chromatic pathway, then wearing amber lenses which block the blue pathway will improve the individual's motion perception ability. If, on the other hand, the major contributor to deficient motion perception is the red/green chromatic pathway, the process becomes more involved. Since the luminance pathway is constructed from information sensed along both the red and green cones, it is necessary to measure the spectral conditions of the environment as well as the location of the individual's equiluminant point and their channel sensitivity to determine the appropriate tint which will allow the luminance pathway to dominate while reducing the influence of the red/green chromatic pathway. In essence, it is possible to change the motion perception ability by analyzing the spectral content of the environment and shifting the spectral content of the retinal image such that the balance of information is received through the luminance channel.

Figure 11A:
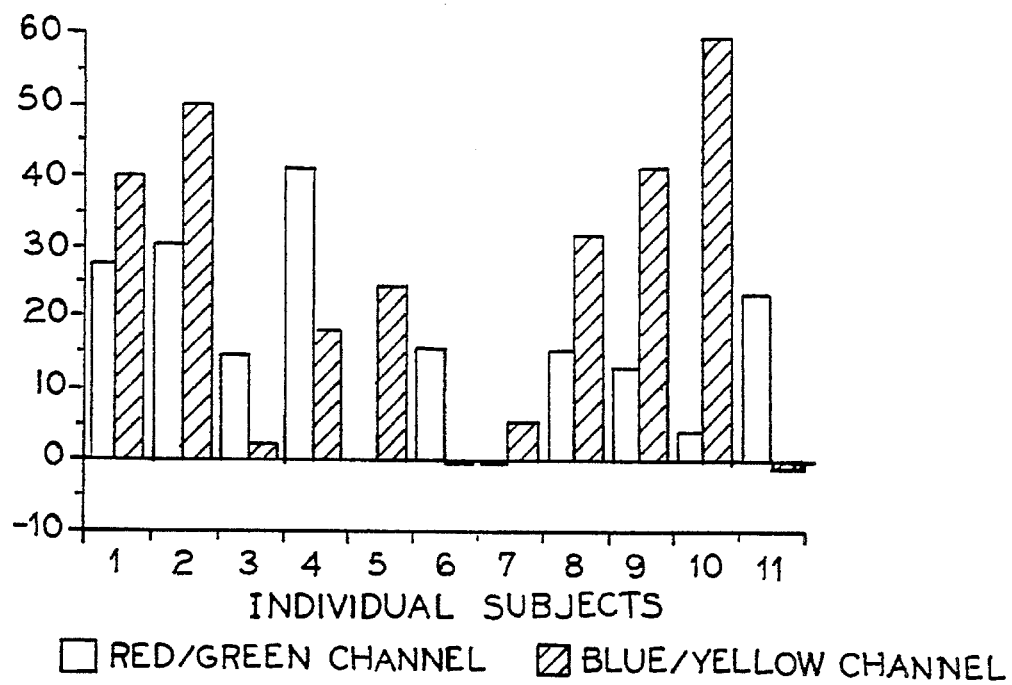
FIGS. 11A and 11B are graphs showing the motion perception of randomly chosen individuals.
Figure 11B:
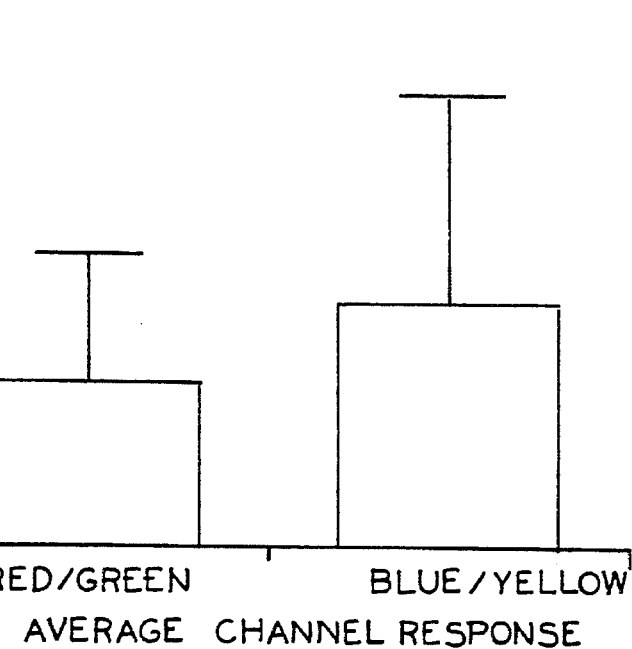

FIG. 11 is a graph of the motion sensitivity of randomly chosen individuals. The individuals show marked difference in both sensitivity to a particular chromatic pathway and variations between the pathways. The chromatic motion diagnostic system can be used to help individuals perceive motion better according to how they perform on this test.

Figure 12:
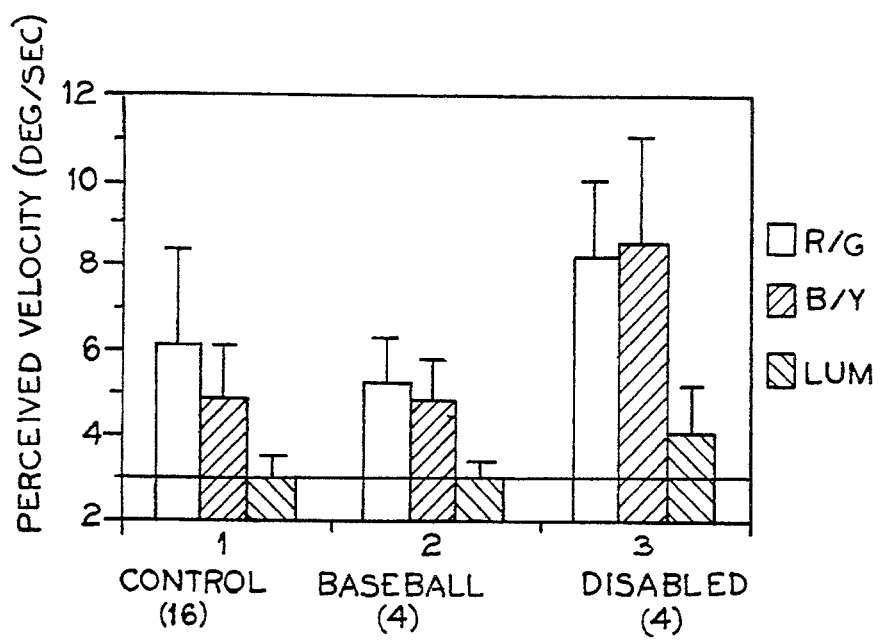
FIG. 12 is a graph of the relative motion perception of three different subject groups along each channel.

FIG. 12 is a graph of the relative motion perception of three different subject groups. The first group is a random sampling of university students. The second group is a number of college varsity baseball players excluding pitchers. The second group was chosen to be self-selected for excellent motion perception. Slow movements are strongly influenced by the chromatic channels. When a baseball player tries to hit a ball, the ball is rapidly moving toward the player. Visually the image of the ball is expanding and translating slowly across the retina. This slow translating motion is exactly the kind of movement that will be most affected. The third group represents a number of disabled readers having dyslexia which demonstrate improvement in reading speed and comprehension when they view the text through a blue tinted filter.

The information in FIG. 12 has several striking features. Motion along the red/green pathway is perceived as moving just about half as fast as the standard luminance motion of three degrees per second for the control group. In other words, the control group had to make the red/green equiluminant pattern 26 move twice as fast on average as the luminance pattern 28. The variance of the control group was quite large among the chromatic pathways indicating that there were widely varying differences between each individual's ability.

Along the blue/yellow chromatic pathway, the baseball players respond almost the same as the random control group. The biggest difference between the control group and the baseball players was in the red/green relative motion measurements. The baseball players perceived the motion significantly closer to the actual motion than the control group. Also, the variation among the baseball players was significantly less for this measurement.

The disabled readers showed the most significant effects. These disabled readers were children about the age of ten who had a better than average IQ. In both the chromatic pathways the disabled readers were significantly different than the controls with a much wider variation. In other words, for the disabled readers, the equiluminant pattern 26 moved at nearly triple the speed of the luminance pattern 28.

The chromatic motion diagnostic system may be used to detect those children who are likely to have this kind of reading disorder such as chromatically affected dyslexia before they begin to read. Intervention at this pre-reading age may help them to overcome or compensate for this problem early.

Figure 13A:
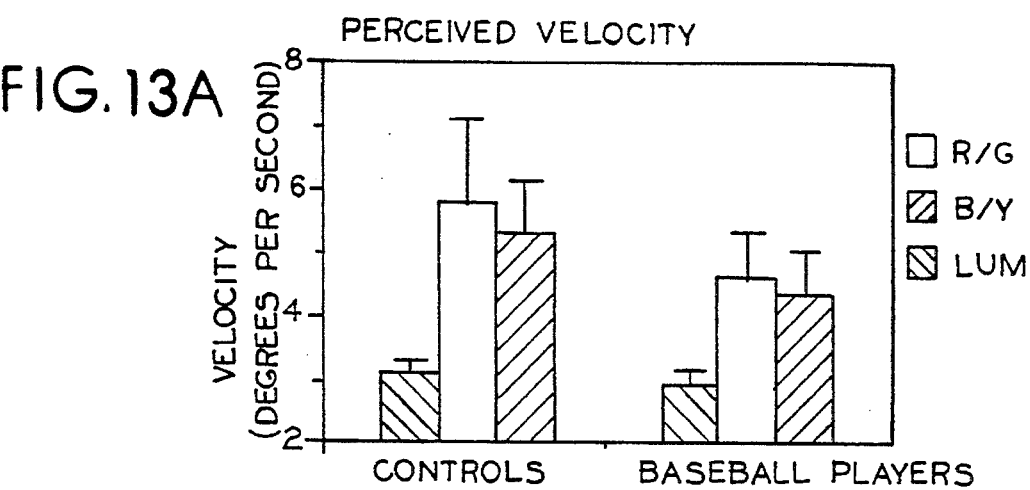
FIGS. 13A and 13B are motion perception comparisons between baseball players and randomly chosen controls.
Figure 13B:
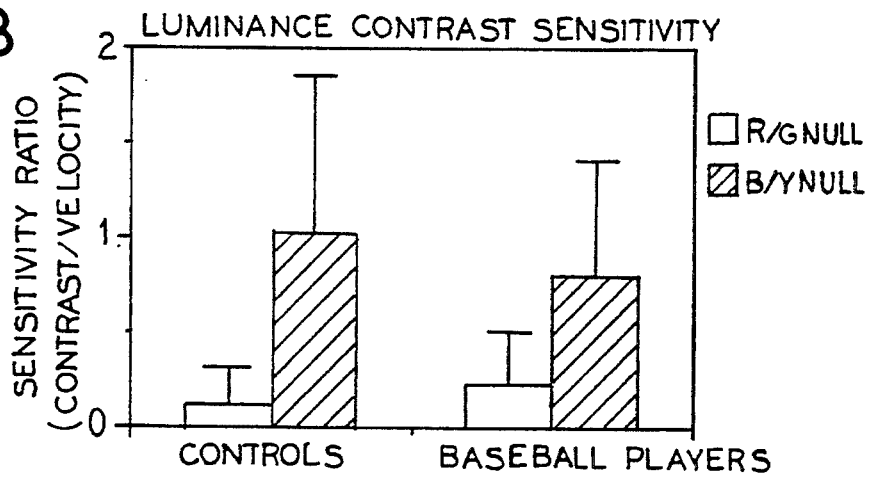

FIGS. 13A and 13B are a comparison between the baseball players and the random controls for the task of the luminance/chromatic pathway balance point. This measurement is an indication of the relative strength of each of the individual pathways to the overall perception of motion. The baseball players were much more sensitive to the luminance content of a moving pattern than the random controls. This shows that not only do the baseball players receive chromatic motion information from the chromatic pathways which is closer to the actual motion, but they seem to be much more sensitive to the luminance pathway for their overall interpretation of motion in the environment.

FIGS. 13A and 13B show that the motion perceived along each of the chromatic pathways was closer to the true motion of three degrees per second for the baseball players. Luminance sensitivity was slightly better (closer to zero) for the control group along the red/green pathway. Luminance sensitivity was better for the baseball players along the blue/yellow pathways.

These results show that baseball players see motion along all of the pathways closer to the motion perceived along the luminance pathway as shown in FIG. 13A. Thus, a change in the illumination will effect the baseball players overall perception of motion less. The sensitivity graph of FIG. 13B indicates that although along the red and green pathways the baseball players and controls are virtually equal, they differ markedly along the blue/yellow chromatic pathway. This means that for the blue/yellow pathway, the baseball players need less luminance in the scene to perceive motion well.

What is claimed is:

1. A method for determining a subject's perceived motion ability utilizing only a chromatic pathway as compared to a luminance pathway, the method comprising the steps of:

a. selecting a first color and a second color which determine the chromatic pathway;

b. determining the equiluminant point of the subject with respect to the first and second colors;

c. providing a first moving pattern of the first color and the second color, the first and second colors of the first pattern being luminant with respect to each other;

d. providing a second moving pattern, the first and second colors of the second pattern being equiluminant with respect to each other;

e. maintaining one of the first and second patterns at a fixed velocity;

f. providing a means for adjusting the velocity of another one of the first and second patterns;

g. having the subject match the appearance of the adjustable velocity to the fixed velocity;

h. determining if a difference exists between the matched adjustable velocity and the fixed velocity, the difference being a determination oil the subject's perceived motion ability utilizing only the chromatic pathway of the subject;

i. providing a motion perception standard; and j. comparing the determination to the standard to evaluate the subject's perceived motion ability.

2. The method of claim 1 wherein the first color is blue and the second color is yellow.

3. The method of claim 1 wherein the first color is red and the second color is green.

4. The method of claim 1 wherein the first and second patterns are sine wave patterns of the first and second colors with the first color 180 degrees out of phase with the second color.

5. A method for determining a subject's perceived motion ability utilizing the red/green and the blue/yellow chromatic pathways, the method comprising the steps of:

selecting a red color and a green color which isolate the red/green chromatic pathway;

determining the equiluminant point of the subject with respect to the red and green colors;

providing a first moving pattern of the red color and the green color, the red and green colors of the first pattern being luminant with respect to each other;

providing a second moving pattern similar to the first pattern, the red and green colors of the second pattern being equiluminant with respect to each other;

maintaining one of the first and second patterns at a fixed velocity;

providing a means for adjusting the velocity of the other of the first and second patterns;

having the subject match the appearance of the adjustable velocity to the fixed velocity;

determining if a difference exists between the matched adjustable velocity and the fixed velocity, the difference being a determination of the subject's perceived motion ability utilizing only the red/green chromatic pathway of the subject;

selecting a blue color and a yellow color which isolate the blue/yellow chromatic pathway;

determining the equiluminant point of the subject with respect to the blue and yellow colors;

providing a third moving pattern of the blue color and the yellow color, the blue and yellow colors of the third pattern being luminant with respect to each other;

providing a fourth moving pattern similar to the third pattern, the blue and yellow colors of the fourth pattern being equiluminant with respect to each other;

maintaining one of the third and fourth patterns at a fixed velocity;

providing a means for the subject to adjust the velocity of the other of the third and fourth patterns;

having the subject match the appearance of the adjustable velocity to the fixed velocity;

determining if a difference exists between the matched adjustable velocity and the fixed velocity, the difference being a determination of the subject's perceived motion ability utilizing only the blue/yellow chromatic pathway of the subject;

providing a motion perception standard; and comparing the determinations to the standard to evaluate the subject's perceived motion ability.

6. The method of claim 5 wherein the step of determining the equiluminant point with respect to the blue and yellow colors includes the step of saturating the red and green cones of the subject.

7. A chromatic motion diagnostic system for determining a subject's perceived motion ability utilizing a chromatic pathway, the system comprising:

a color projector;

a pattern generation system in electrical communication with the color projector, the pattern generation system generating moving patterns on the color projector;

means for adjusting the patterns generated on the color projector, the adjustment means in electrical communication with the pattern generation system and the color projector, the adjustments including velocity, luminosity, and contrast of the patterns.

8. The motion diagnostic system of claim 7 further comprising a monitor calibration circuit.

9. The motion diagnostic system of claim 8 wherein the monitor calibration circuit comprises a photometer and memory means in electrical communication with the pattern generation system, the pattern generation system generating a calibration pattern onto a specific location on the projector, the photometer being located at the specific location and the photometer measuring the calibration pattern intensities, the measured intensities being compared to expected intensities stored in the memory means, the monitor calibration circuit adjusting the pattern generation system to match the measured intensities to the expected intensities.

10. The motion diagnostic system of claim 7 wherein the pattern generation system is a computer.

11. The motion diagnostic system of claim 7 wherein the adjustment means is a mouse.

12. The motion diagnostic system of claim 7 wherein the color projector is a color monitor.

13. The motion diagnostic system of claim 7 further comprising means for isolating the blue/yellow chromatic pathway.

14. The motion diagnostic system of claim 13 wherein the isolating means comprises a blue filter having a spectral cutoff point of about 550 nanometers, a screen, the filter and the screen being positioned between the subject and the color projector, and an amber light source positioned to reflect amber light from the screen into the subject's eyes, the reflected amber light being of sufficient intensity to saturate the red and green cones of the subject's eyes.

15. The motion diagnostic system of claim 13 wherein the isolating means comprises a dichroic filter.

16. A method for comparing a subject's perceived motion ability utilizing the red/green chromatic pathway versus the luminance pathway, the method comprising the steps of:

a) determining the equiluminant point of the subject with respect to the colors red and green;

b) providing a first moving pattern of the colors red and green, the red and green colors of the first pattern being luminant with respect to each other;

c) providing a second moving pattern similar to the first pattern, the red and green colors of the second pattern being equiluminant with respect to each other, the second pattern being superimposed over the first pattern;

d) maintaining the first and second patterns at a first fixed velocity but in opposite directions;

e) setting one of the first and second patterns at a first fixed contrast;

f) providing the subject with means for adjusting a reference contrast of the other of the first and second patterns;

g) having the subject adjust the reference contrast of the other of the first and second patterns until the combination of the first and second patterns appears to stop and measuring a first reference contrast;

h) selecting a second fixed velocity for the patterns and repeating step g to obtain a second reference contrast;

i) determining the ratio between the difference in the first and second reference contrasts to the difference in the first and second velocities, the ratio being a measure of the sensitivity of the overall motion perception to motion information from the red/green chromatic pathway;

j) providing a pathway balance standard ratio; and k) comparing the determined ratio to the standard ratio to evaluate the subject's perceived motion ability along the red/green chromatic and luminance pathways.

17. A method for comparing a subject's perceived motion ability utilizing the blue/yellow chromatic pathway versus the luminance pathway, the method comprising the steps of:
   a) determining the equiluminant point of the subject with respect to the colors blue and yellow;
   b) providing a first moving pattern of the colors blue and yellow, the blue and yellow colors of the first pattern being luminant with respect to each other;
   c) providing a second moving pattern similar to the first pattern, the blue and yellow colors of the second pattern being equiluminant with respect to each other, the second pattern being superimposed over the first pattern;
   d) maintaining the first and second patterns at a first fixed velocity but in opposite directions;
   e) setting one of the first and second patterns at a first fixed contrast;
   f) providing the subject with means for adjusting a reference contrast of the other of the first and second patterns;
   g) having the subject adjust the reference contrast until the combination of the first and second patterns appears to stop and measuring a first reference contrast;
   h) selecting a second fixed velocity for the patterns and repeating step g to obtain a second reference contrast;
   i) determining the ratio between the difference in the first and second reference contrasts to the difference in the first and second velocities, the ratio being a measure of the sensitivity of the overall motion perception to motion information from the blue/yellow chromatic pathway;
   j) providing a pathway balance standard ratio; and
   k) comparing the determined ratio to the standard ratio to evaluate the subject's perceived motion ability along the blue/yellow chromatic and luminance pathways.

18. A method for comparing a subject's perceived motion ability utilizing a chosen chromatic pathway versus the luminance pathway, the method comprising the steps of:
   a) determining the equiluminant point of the subject with respect to a first and second color for the chosen pathway;
   b) providing a first moving pattern of the first and second colors, the colors of the first pattern being luminant with respect to each other;
   c) providing a second moving pattern similar to the first pattern, the first and second colors of the second pattern being equiluminant with respect to each other, the second pattern being superimposed over the first pattern;
   d) maintaining the first and second patterns at a first fixed velocity;
   e) setting one of the first and second patterns at a first fixed contrast;
   f) providing the subject with means for adjusting a reference contrast of the other of the first and second patterns;
   h) providing a third pattern of the first and second colors, the colors of the third pattern being luminant with respect to each other;
   i) maintaining the third pattern at a fixed velocity slower than the first velocity but faster than the subject's perceived velocity of the second pattern;
   j) having the subject adjust the second reference contrast of the other of the first or second pattern until the first and second patterns appear to match the third pattern in velocity and measuring a first reference;
   k) selecting a second fixed velocity for the first and second patterns;
   l) repeating step j to obtain a second reference contrast; and
   m) determining the ratio between the difference in the first and second reference contrasts to the difference in the first and second velocities, the ratio being a measure of the sensitivity of the overall motion perception to information from the chosen chromatic pathway.

19. A method for comparing a subject's perceived motion ability utilizing the blue/yellow chromatic pathway versus the luminance pathway, the method comprising the steps of:
   a) providing a first moving pattern of blue and a color which does not include blue;
   b) providing a second moving pattern of two colors which are luminant with regard to each other;
   c) maintaining one of the first and second patterns at a first fixed velocity and the other at another fixed velocity, with the velocity of the first pattern being greater than the second;
   d) providing isolating means for adjustably isolating the blue/yellow chromatic pathway from the first pattern;
   e) having the subject adjust the isolating means until the patterns appear matched in velocity, the adjustment providing a first reference measurement;
   f) selecting a second fixed velocity for either the first or second pattern;
   g) having the subject adjust the isolating means until the patterns appear matched in velocity, the adjustment providing a second reference measurement; and
   h) determining the ratio of the differences in the first and second reference measurements to the differences in the first and second velocities, the ratio being a measure of the sensitivity of the overall motion perception to motion information for the blue/yellow chromatic pathway.

20. The method of claim 19 wherein the isolating means includes a blue filter between the subject and the first pattern and an amber light source positioned to direct light into the subject's eyes, the intensity of the amber light source being adjustable.

21. A method of treating disabilities relating to motion perception, the method comprising the steps of:
   determining the subject's perceived motion ability utilizing the red/green and blue/yellow chromatic pathways as described in claim 5;
   comparing the subject's perceived motion ability utilizing the red/green chromatic pathway versus the luminance pathway as described in claim 16;
   comparing the subject's perceived motion ability utilizing the blue/yellow chromatic pathway versus the luminance pathway as described in claim 17;
   determining which chromatic pathway interferes with the subject's motion perception abilities; and
   modifying the spectrum of the light impinging upon the subject's eyes to minimize the effect of the interfering pathway.

22. The method of claim 21 wherein the disability is dyslexia where the individual demonstrates improvement in comprehension and reading speed with color changes and the motion perception standard and the pathway balance standard are derived from the general population.

23. The method of claim 22 wherein the step of modifying the spectrum further comprises providing tinted lenses to the subject which filter out the interfering pathway.

24. The method of claim 1 wherein the first color is red and the second color is green, and further comprising the steps of performing steps a–h for blue and yellow colors.

25. The method of claim 1 further comprising, after step h, the steps of:

k) repeating step d with the substep of superimposing the second pattern over the first pattern;

l) maintaining the first and second patterns at a first fixed velocity;

m) setting one of the first and second patterns at a first fixed contrast;

n) providing the subject with means for adjusting a reference contrast of the other of the first and second patterns;

o) providing a third pattern of the first and second colors, the colors of the third pattern being luminant with respect to each other;

p) maintaining the third pattern at a fixed velocity slower than the first velocity but faster than the subject's perceived velocity of the second pattern;

q) having the subject adjust the second reference contrast of the other of the first or second pattern until the first and second patterns appear to match the third pattern in velocity and measuring a first reference;

r) selecting a second fixed velocity for the first and second patterns;

s) repeating step j to obtain a second reference contrast; and t) determining the ratio between the difference in the first and second reference contrasts to the difference in the first and second velocities, the ratio being a measure of the sensitivity of the overall motion perception to information from the chosen chromatic pathway.

26. A method of determining components of a subject's perceived motion ability comprising the steps of:

a) generating at least two patterns to be displayed on a display device, each pattern having parameters that include velocity, luminosity and contrast;

b) maintaining a first magnitude one of the parameters of a first one of the patterns fixed;

c) having the subject adjust a second magnitude of a corresponding parameter in another one of the patterns with reference to the first one of the patterns; and d) determining the difference between the fixed first magnitude and the adjusted second magnitude.

* * * * *